(12) United States Patent
Xu et al.

(10) Patent No.: US 7,022,101 B2
(45) Date of Patent: Apr. 4, 2006

(54) METHOD AND APPARATUS FOR CLEANSING THE COLON

(76) Inventors: Haohan Xu, Floor 6 (E), Building 2, Guangxianxiaoqu, Baguasanlu, Futian District, Shenzhen (CN), 518029; Tao Jin, Floor 6 (E), Building 2, Guangxianxiaoqu, Baguasanlu, Futian District, Shenzhen (CN), 518029

( * ) Notice: Subject to any disclaimer, the term of this patent is extended or adjusted under 35 U.S.C. 154(b) by 380 days.

(21) Appl. No.: 10/322,644

(22) Filed: Dec. 19, 2002

(65) Prior Publication Data
US 2003/0195481 A1 Oct. 16, 2003

(30) Foreign Application Priority Data
Apr. 12, 2002 (CN) .......................... 02115088 A
Apr. 12, 2002 (CN) ........................ 02226864 U

(51) Int. Cl.
*A61M 1/06* (2006.01)

(52) U.S. Cl. ........................................... 604/73; 604/28
(58) Field of Classification Search .............. 604/19, 604/21, 27–36, 500, 73, 275–277, 290, 48, 604/65, 67, 113, 114, 118, 244–247, 257, 604/262, 82–85, 131, 151, 271, 355–356, 604/323, 326, 322; 4/443–445, 420–420.4, 4/420.1–420.5
See application file for complete search history.

(56) References Cited
U.S. PATENT DOCUMENTS
4,326,837 A 4/1982 Gilson et al.
4,624,625 A 11/1986 Schrenker
4,626,239 A * 12/1986 Ardizzone ................. 604/31
5,951,511 A * 9/1999 Lowder ..................... 604/73

FOREIGN PATENT DOCUMENTS
DE 19623537 12/1997

* cited by examiner

*Primary Examiner*—Nicholas D. Lucchesi
(74) *Attorney, Agent, or Firm*—DLA Piper Rudnick Gray Cary US LLP

(57) ABSTRACT

The present invention is to provide a method for cleansing the colon of a patient, which comprises the steps of producing a lavage water at a temperature of 20–38° C. by an apparatus connected to a water resource; contacting an cleansing instrument of the apparatus with the anus of the patient, said the cleansing instrument having a curve plane with a cleansing opening, and said curve plane fitting to the portion of the patient's body close to the anus so that the cleansing opening can completely fit the anus; directing the lavage water into the anal canal of the patient under a predetermined pressure in coordination with the abdomen-contracting action of the patient; removing the cleansing instrument when the patient feels abdominal distension; and discharging the feces in the colon out of the body. The invention also provides an apparatus for cleansing the colon of the patient, including a housing, a heating device, a cleansing device having a cleansing opening fitted to the portion of the patient's body close to the anus; and controlling means for controlling the temperature of water in the heating device.

8 Claims, 6 Drawing Sheets

US 7,022,101 B2

METHOD AND APPARATUS FOR CLEANSING THE COLON

BACKGROUND OF THE INVENTION

1. Field of the Invention

This invention is directed to a medical device and a method of using the same, more particularly, to an apparatus and method for cleansing the colon of a patient.

2. Background of the Technology

Many people, particularly those who are elderly, have difficulties in bowel movement, such as constipation. Drugs administration and colonic irrigation have been used to treat these diseases, and the colonic irrigation is the only way for some severe cases.

However, although the prior art has disclosed many devices for colonic irrigation, all the devices have an insertion member that needs to be inserted into the body of the patient when operated. Apparently, the patient will feel uncomfortable when such an operation undertakes. Accordingly, it is desirable to create an apparatus that can introduce water into the body without any insertion members. The present invention is hereby provided.

SUMMARY OF THE INVENTION

One object of the invention is to provide a method for cleansing the colon of a patient, said method comprising:

a) producing a lavage liquid by an apparatus connected to a water resource;

b) contacting an cleansing instrument of the apparatus with the anus of the patient, the cleansing instrument having a curve plane with a cleansing opening, and the curve plane fitting to the portion of the body close to the anus so that the cleansing opening can be completely matched with the anus;

c) directing the lavage liquid into the anal canal of the patient under a predetermined pressure in coordination with the abdomen-contracting action of the patient;

d) removing the cleansing instrument when the patient feels abdominal distension; and e) discharging the feces in the colon out of the body.

In the method of the invention, the lavage liquid in general is water.

Another object of the invention is to provide an apparatus for cleansing the colon of the patient, which comprises a housing having an inlet and an outlet; a heating device disposed at the lower portion within the housing, including a tubular container comprising a water inlet and a water outlet, and a heater; a cleansing device connected to the outlet of the housing, including an cleansing instrument comprising an upper surface having a curve plane with an opening matched with the portion of the body close to the anus so that when the curve plane contacts the portion, the opening exactly matches the anus; and control means for controlling the temperature of water in the heating device.

The apparatus of the invention may further comprise an ozonizer which includes a casing disposed at the upper portion of the housing; an ozonizing tube arranged in the casing having a gas outlet connected to the water outlet through a delivery conduit; and a pumping means disposed within the casing for delivering the ozone generated from the ozonizing tube to the water outlet.

Compared with the prior art, the invention may directly introduce the lavage liquid into the body without insertion of any foreign matters to thus avoid any stimulation to the body of the patient. The ozonizer and the heating device in the apparatus can provide a proper lavage liquid for cleaning the anus or vulva of the patient. The apparatus of the invention is easily operated by the patient himself in no need of the assistant.

BRIEF DESCRIPTION OF THE INVENTION

The present invention is described in detail in combination with the drawings.

Figure 1:
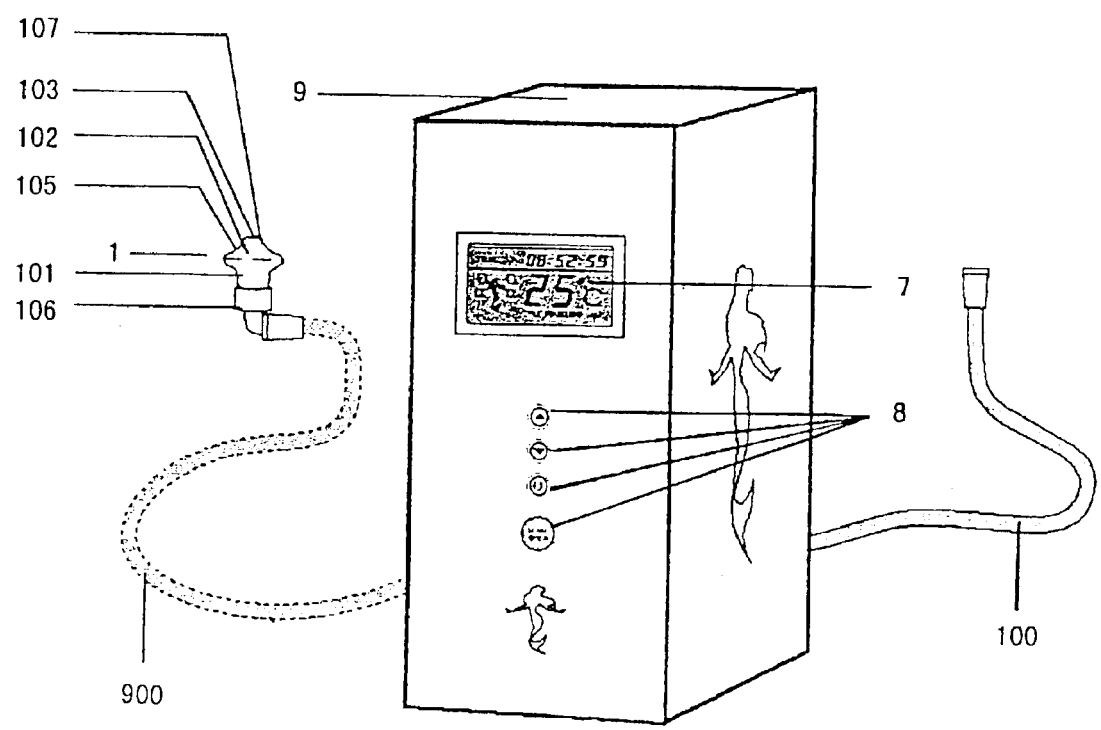
FIG. 1 is a schematic view of an apparatus according to the invention.
Figure 2:
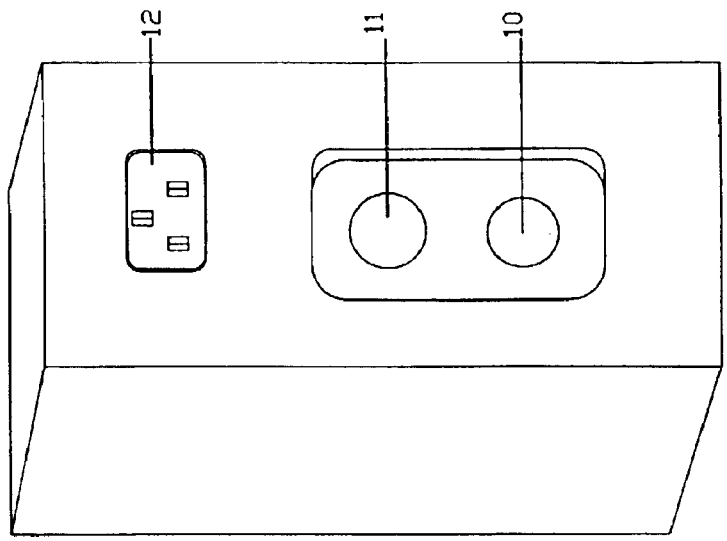
FIG. 2 shows a housing of the apparatus according to the invention.

Referring to FIGS. 1 and 2, a housing 9 of the apparatus of the invention is shown. On the surface of the housing 9 is arranged a display 7 that shows data of the temperature of water and time of the operation. An outlet 11 of a cleansing device 1 is connected to the housing 9 through a connection hose 900. At one sidewall of the housing 9 are set of a couple of control switches 8. An inlet 10 of the housing is connected to a water resource (not shown) through a conduit 100. Reference numeral 12 represents a socket for power supplying.

Figure 3:
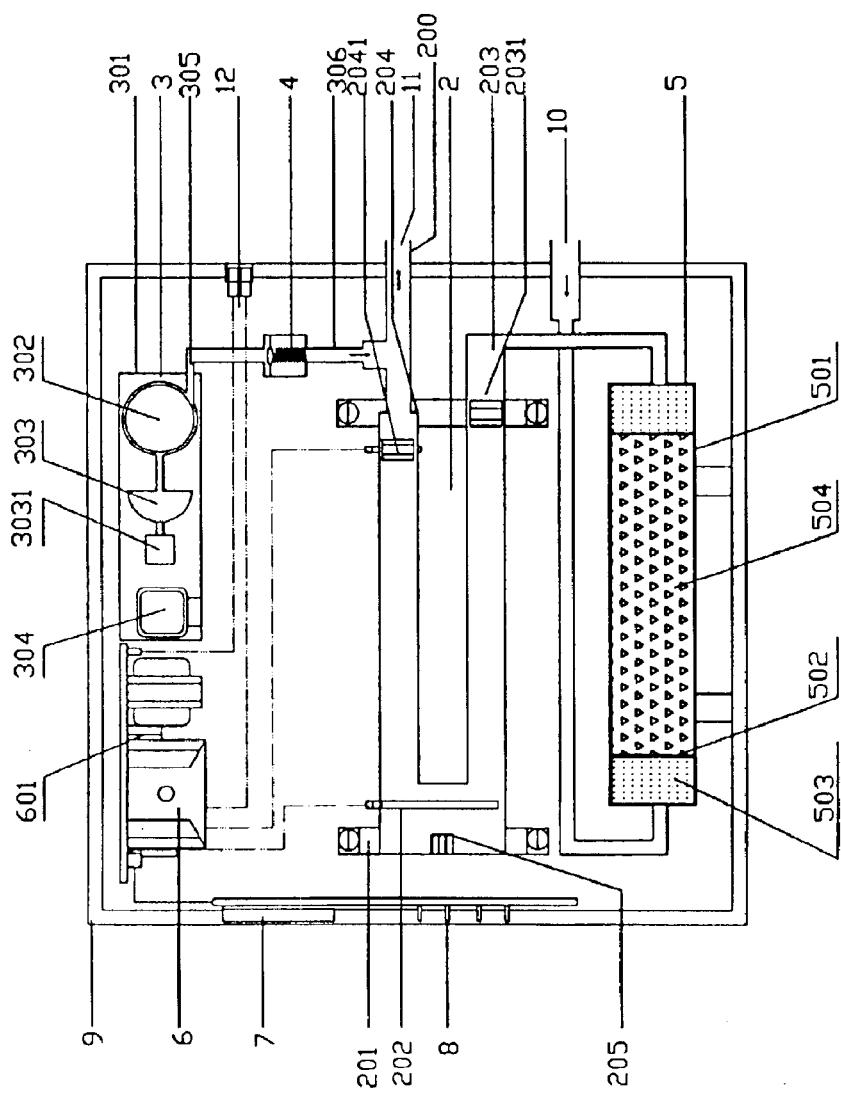
FIG. 3 is a cross sectional view of one embodiment of the housing according to the invention.

FIG. 3 is a cross-sectional view of the housing 9 that shows an embodiment of the invention. Water as the lavaging liquid is introduced through the inlet 10 into a filtering device 5. The filtering device 5 includes a casing 501. From the two ends of the casing 501 are successively disposed two filtering layers 503 and two filtering meshes 502. Charcoal layer 504 is disposed between two filtering meshes 502. Thus, those chlorides and fluorides as well as other impurities existing in water can be removed before water enters a heating device 2. The filtered water from the filtering device 5 is then introduced into the heating device 2 via a cold water inlet 203. A pressure-control switch 2031 is set within the cold water inlet 203. An electrically heating tube or electrically heating wires or those conventionally used in the art can be used as a heater 202 for heating water in the heating device 2. In the invention, an electrically heating film coated on a quartz tube is preferably used. Heated water is discharged out of the heating device 2 from a hot water outlet 204. Close to the water outlet 204 is set a temperature-sensitive probe 2041. A controlling means 6 controls the pressure of water in the water inlet 203 and the temperature of water in the water outlet 204.

In the present invention, the temperature of water in the heating device 2 can be regulated according to the patient's situation and demand. The temperature of water is generally regulated at a range from 20° to 38° C., depending on the condition of the patient. The switch 2031 is provided to avoid water in the heating device being used up. When the pressure of water in the water inlet 203 is lower than 0.2 Mpa but higher than 0.02 Mpa, the switch can turn the power off. When the temperature of the water in the water outlet 204 reaches at 38° C., the controlling means 6 renders the heater 202 off. An LCD disposed at the surface of the housing 9 as the display 7 is connected to the controlling means 6.

A magnetizing member 205 may be set in a water channel 202 in the heating device 2, so that the magnetized water can be produced in the apparatus.

Figure 8:
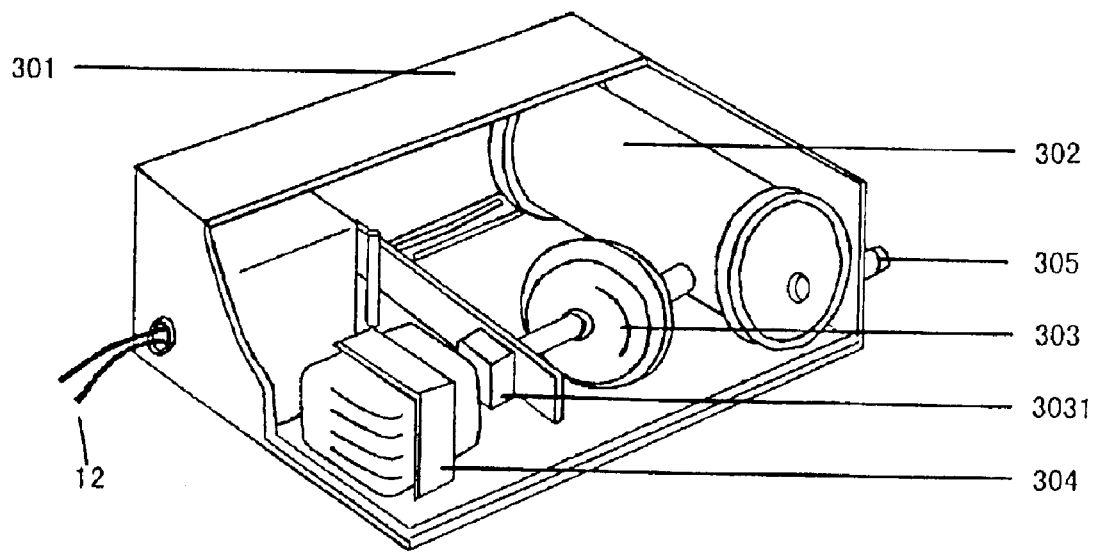
FIG. 8 is a partially exploded view of an ozonizer of the apparatus according to the invention.

As show in FIG. 3, an ozonizer 3 is further provided at the upper portion within the housing 9. The ozonizer 3 produces ozone that is mixed with the heated water from the heating device 2. The water containing ozone can kill bacteria in the colon and is better for cleansing the anus and the vulva of the patient. Referring to FIGS. 3 and 8, the ozonizer 3 comprises a casing 301, an ozonizing tube 302, a gas pump 303 and a magnet 3031, an electro-magnetic coil 304, and a gas outlet 305. As shown in FIG. 8, when the ozonizing tube 302 is on, air between two electrodes (not shown) disposed in the ozonizing tube is breakdown to thereby produce ozone. The electro-magnetic coil 304 is matched with the magnet 3031 to drive the pump 303 to direct the ozone out of the tube 302 from the gas outlet 305. The gas outlet 305 is connected to an outlet conduit 200 in the heating device 2 through a delivery conduit 306 controlled by a one-way valve 4. The ozonizer 3 is controlled by the control means 6 through controlling the power supplying of the electro-magnetic coil.

In the present invention, the heating device also provides a magnet 205 attached to the inner wall of the tubular container 210 to generate a magnetized water for enhancing the effect of the cleansing.

Figure 7:
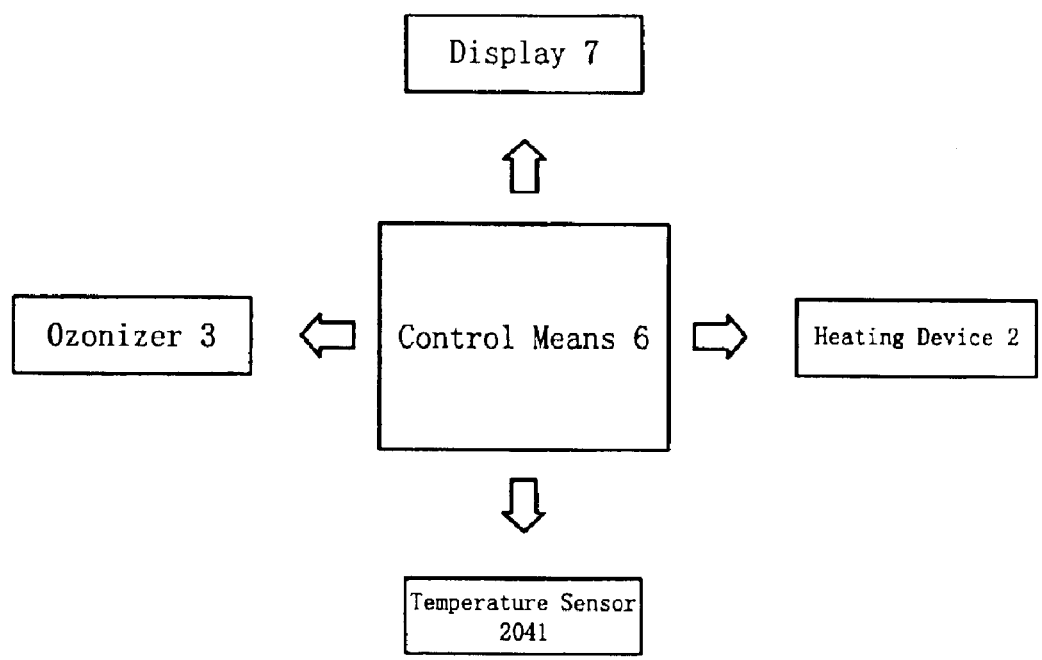
FIG. 7 shows how a control means of the invention works.

Referring to FIG. 3, the control means 6 may comprise a control circuit 601 installed within the housing 9. LCD display 7 and the control switch 8 embedded into the housing are connected to an output port and an input port of the circuit 601, respectively. The control circuit 601 can be implemented by a single chip or those known by the skilled in the art. The control circuit 601 is connected to the ozonizer 3 and the heating device 2, and control them as shown in FIG. 7.

Figure 9:
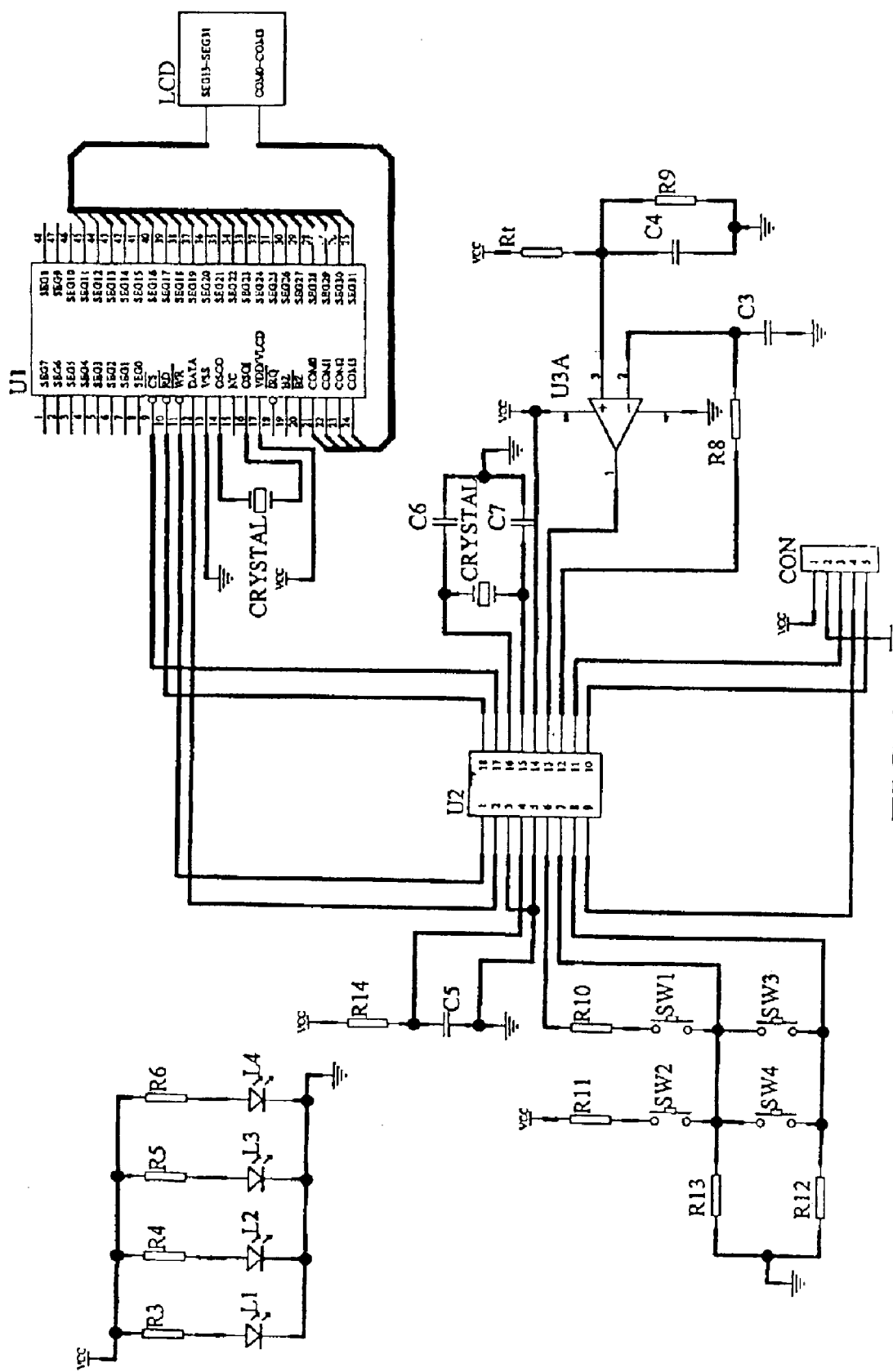
FIG. 9 is a circuit diagram showing an embodiment of the control means according to the invention.

FIG. 9 shows an embodiment of the control circuit 601 including a single chip of the apparatus according to the invention. When SW1 is pressed, the LCD is initiated to display the temperature of water at the present. SW3 and SW4 control the heating device 2 and SW2 controls the ozonizer 3.

Figure 4:
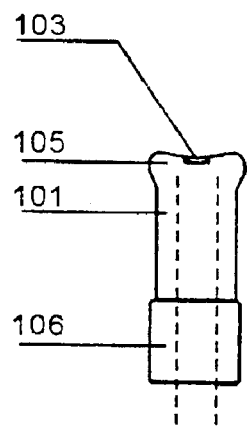
FIG. 4 is a view showing a cleansing instrument of the cleansing device of the apparatus according to the invention.
Figure 5:
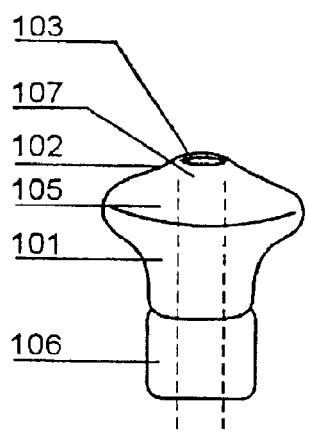
FIG. 5 shows an alternative embodiment of the cleansing instrument shown in FIG. 4.
Figure 6:
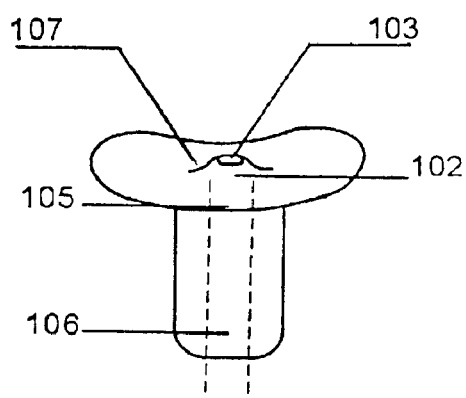
FIG. 6 shows another alternative embodiment of the cleansing instrument shown in FIG. 4.

FIGS. 4, 5 and 6 respectively show three embodiments of the cleansing instrument 101 of the cleansing device 1. Referring to FIGS. 1, 4, 5 and 6, the cleansing device 1 includes a connection member 106 connected to the cleansing instrument 101. The connection member 106 is connected to the outlet 11 of the housing 9 through the connection hose 900. The cleansing instrument 101 shown in FIGS. 5 and 6 includes an upper surface 102 having a curve plane 105 from which a tapered project 107 is extended upwards and is terminated by a cleansing opening 103. The tapered project 107 is formed in such a shape that it can fully fit to the portion of the patient's body close to the anus to make the opening 103 completely fit the anus.

The apparatus of the present invention operates as follows.

Figure 11:
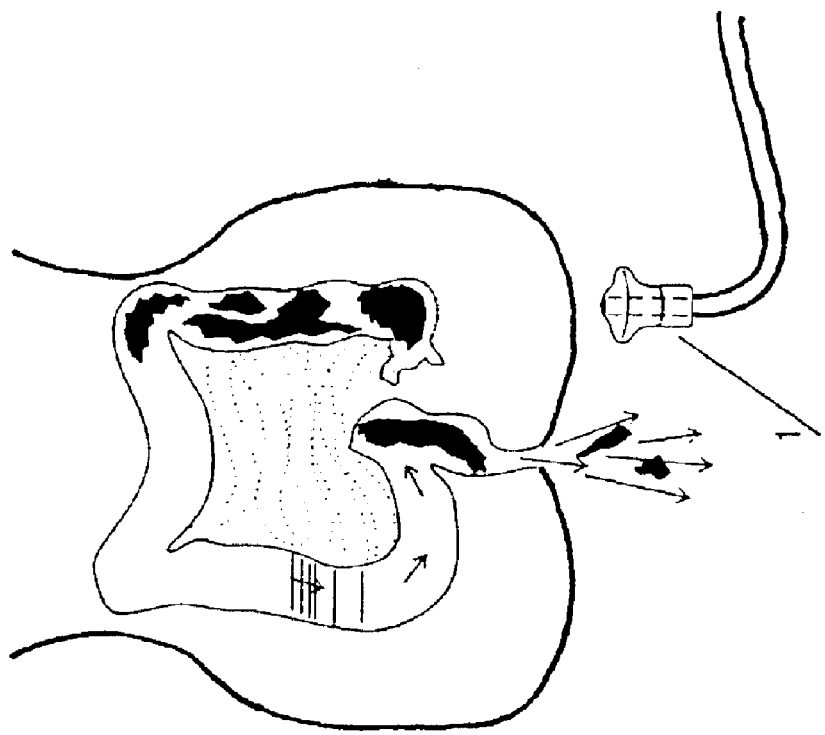
FIG. 11 a schematic view illustrating the cleansing operation of the instrument while it is removed from the anus of the body.
Figure 10:
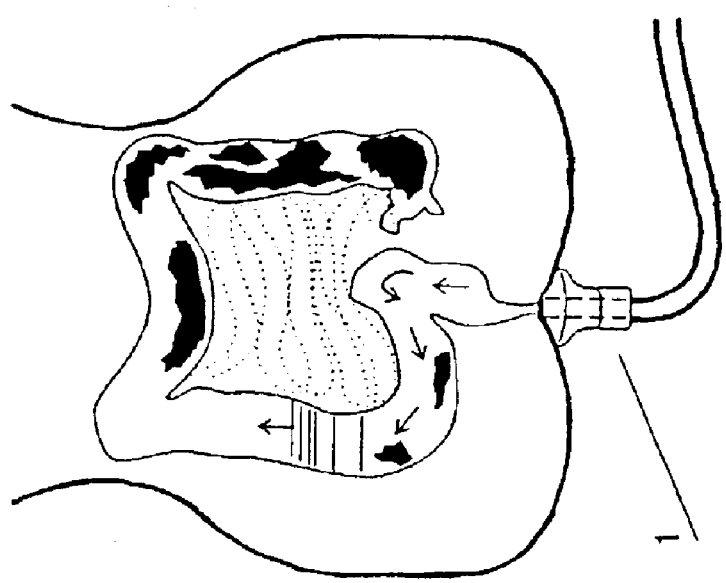
FIG. 10 is a schematic view illustrating the cleansing operation of the instrument while it is attached to the anus of the body.

Water from a resource is introduced into the filtering device 5 and the heating device 2. The patient may adjust the temperature of water upon his demand. Referring to FIGS. 10 and 11, the patient holds the cleansing device 1 and contacts the cleansing instrument 101 to the anus. Under the pressure of water coming from the water resource and the pressure difference produced by itself (for example, the diameter of the cleansing opening 103 being smaller than that of the inlet), the filtered and heated water is then injected into the colon of the patient in coordination with the motion of abdomen contracting, where the water loosens and mixes with fecal accumulation. When the patient has a feeling of bowel movement, the cleansing instrument 101 is taken away and the feces in the colon are discharged. This performance can be taken repeatedly as required. In general, the treatment takes 10–20 seconds one time.

If required, the ozonizer is initiated to produce a lavage water containing ozone that may be used to cleanse the anus or vulva after cleansing the colon.

During the operation of the cleansing, the flow of the cleansing instrument water may stimulate the colonic muscle close to the anus and enhance the reaction of contract of the muscle so that bowel movement can be readily taken.

Clinical Experiments

Two groups of voluntary patients were tested with the apparatus of the invention, each having 55 patients. The tested results are shown as follows.

| Items | Curative Effect (%) |
|---|---|
| Joint of Descendens Colon and Sigmoideum Colon | 100 |
| Splenic Flexure of Colon | 96.4 |
| Hepatic Flexure of Colon | 90.9 |
| Ileocecum | 83.6 |

Although during the treatment, 87.3% of patients felt abdominal distension, 27.3% of patients felt abdominal pain and 5.5% of patients got palpitation, all of them could bear conditions that disappeared soon after the treatment.

The above embodiments and description are merely used to illustrate, but not intended to limit, the invention. Any modifications and variations to the invention without departure from the spirit of the invention should fall within the scope of the appended claims.

What is claimed is:

1. A method for cleansing the colon of a patient without inserting a device into the patient's body, comprising the steps of:
    a) producing a lavage liquid at a predetermined temperature through an apparatus connected to a resource;
    b) contacting a cleansing instrument of said apparatus with the anus of the patient, said cleansing instrument having a curve plane with a cleansing opening, and said curve plane having such a shape that said cleansing opening can completely fit the anus;
    c) directing said lavage liquid into the anal canal of the patient under a predetermined pressure in coordination with the abdomen-contracting action of the patient;
    d) removing said cleansing instrument when the patient feels abdominal distension; and
    e) discharging the feces in the colon out of the body.

2. A method according to claim 1, further including the step of ozonizing said lavage liquid with an ozone generated from an ozonizer disposed within said housing.

3. A method according to claim 1, wherein said predetermined temperature is at from 20° to 38° C, and said pressure is from 0.02Mpa to 0.2Mpa.

4. A method according to claim 2, further including the step of cleaning the portion of the body close to the anus or the vulva of the patient after the step e).

5. A method according to claim 1, further including the steps of repeating the steps of c), d) and 3).

6. A method according to claim 2, further including the step of repeating the steps of c), d) and e).

7. A method according to claim 3, further including the step of repeating the steps of c), d) and e).

8. A method according to claim 4, further including the step of repeating the steps of c), d) and e).

* * * * *